United States Patent [19]

Inaba et al.

[11] Patent Number: 5,334,497
[45] Date of Patent: Aug. 2, 1994

[54] METHOD OF FEEDING A SUBSTRATE INTO TUBULAR BIOREACTOR

[76] Inventors: Hideki Inaba, Seimei-ryou, 1-25-5, Iwase, Kamakura-shi, Kanagawa; Isao Endo, 5-7-6, Honda, Kokubunji-shi, Tokyo; Teruyuki Nagamune, 2nd Chuou Mansion, 404, 2-16-74, Chuou, Kamifukuoka-Shi, Saitama; Susumu Tachikawa, c/o Hiratsuka Laboratory, 63-30, Yuuhigaoka, Hiratsuka-shi, Kanagawa, all of Japan

[21] Appl. No.: 786,819

[22] Filed: Nov. 4, 1991

Related U.S. Application Data

[63] Continuation-in-part of Ser. No. 385,698, Jul. 27, 1989, abandoned.

Foreign Application Priority Data

Dec. 13, 1988 [JP] Japan ................. 63-312792

[51] Int. Cl.$^5$ .......................... C12Q 3/00; C12M 1/36
[52] U.S. Cl. ............................. 435/3; 435/41; 435/289; 435/311; 435/316; 435/813
[58] Field of Search ............... 435/243, 287, 291, 313, 435/316, 813, 819, 3, 41, 289, 311; 210/85, 87, 258, 321.87, 500.26, 636

[56] References Cited

U.S. PATENT DOCUMENTS

| | | | |
|---|---|---|---|
| 3,186,917 | 6/1965 | Gerhardt et al. | 435/813 |
| 3,767,534 | 10/1973 | Miura | 435/243 |
| 3,847,748 | 11/1974 | Gibson et al. | 435/813 |
| 3,926,737 | 12/1975 | Wilson et al. | 435/290 |
| 3,926,738 | 12/1975 | Nyiri et al. | 435/290 |
| 3,969,190 | 7/1976 | Hise et al. | 435/313 |
| 4,181,576 | 1/1980 | Malick | 435/313 |
| 4,468,329 | 8/1984 | Shaldon et al. | 210/85 |
| 4,746,615 | 5/1988 | Buchholz et al. | 435/813 |
| 4,889,812 | 12/1989 | Guinn et al. | 435/813 |
| 4,923,598 | 5/1990 | Schäl | 210/87 |

*Primary Examiner*—Robert J. Warden
*Assistant Examiner*—T. A. Trembley
*Attorney, Agent, or Firm*—Hoffman, Wasson & Gitler

[57] ABSTRACT

A method of feeding substrates into a tubular bioreactor incorporating a reacting vessel and a separating membrane in which the reaction and separation or collection can be continuously and surely effected in the same vessel with high efficiency.

7 Claims, 3 Drawing Sheets

METHOD OF FEEDING A SUBSTRATE INTO TUBULAR BIOREACTOR

This application is a continuation-in-part of Ser. No. 385,698 filed Jul. 27, 1989, now abandoned.

FIELD OF THE INVENTION

The present invention relates to a method of feeding substrate(s) into a tubular bioreactor incorporating a reacting vessel and a separating membrane, in which reaction and separation (or collection) can be continuously and surely effected in the same vessel with high efficiency.

The wording "tubular bioreactor" as used herein describes a reactor in which a flow containing a biologically active catalyst (hereinafter referring to as "biocatalyst") and reacting agent(s) can be circulated in a closed tubular circuit in loop form ("circular structure"). The biocatalyst and reacting agent(s) react together and the resulting material(s) or useful product(s) can be discharged through membrane module(s) mounted on, and at least in place of, at least a portion of the wall of the circular structure, in the form of tubing or forming a portion of the wall.

DESCRIPTION OF THE PRIOR ART

In the prior art, the reaction using biocatalysts such as microorganism(s) and enzyme(s) is difficult to carry out in continuous form, and there has been little success in commercialization of such a continuous biocatalyzed process. There are many reasons for this lack of success, for example, it is difficult to adjust the concentration of the microorganisms and it is difficult to recover and reuse costly enzyme.

Reactors in loop form for carrying out a suspension polymerization, which is a fraction reaction apparatus in open form have been investigated. In addition, reactors in which a separation operation is not necessary have been investigated. However, these concepts do not correspond to the closed loop reactor which is used for the present invention.

Examples of the prior art membrane bioreactors are shown in FIGS. 1 and 2. These are shown as fermentation vessels and independent membrane modules connected together. The common members shown in FIGS. 1 and 2 have the same numeral indications. The fermentation liquid is recycled by a circulating pump 2 from a fermentation vessel 1 to a membrane module 4 for filtration, and the retentate is returned to a fermentation vessel 1. The liquid passing through the membrane is discharged from a tube 10. The pressure at the inlet of the membrane 4 and the pressure at the outlet of the membrane 4 are respectively measured by the pressure gauges 3 and 5. The filtration condition is controlled by adjusting the flow rate of a circulating pump 2 and a pressure valve 6.

In those systems, the feed of the substrates is controlled as follows: In FIG. 1, a flow rate adjusting valve 12 is operated by a computer 13 on the basis of the measurement of a flow rate of the liquid by a flow measurement means 11, so as to regulate the flow passing through a membrane 4. On the other hand, the liquid level in a fermentation vessel 1 is measured by a level sensor 7, while a level controller 8 operates a feed pump 9 intermittently on the basis of measurements by the level sensor 7, so as to maintain a liquid amount in the fermentation vessel 1 at a given value. In FIG. 2, a feed pump 9 is operated to maintain the flow rate at a certain level, and a level controller 8 measuring a level in a fermentation vessel 1 will operate a valve 14 for discharging a filtrate on the basis of measured level in the vessel 1.

SUMMARY OF THE INVENTION

The inventors have been investigating an efficient process for a biocatalyzed reaction, and at last have developed a method for continuously and constantly feeding substrate(s) into a new bioreactor. The new bioreactor is a tubular united bioreactor incorporating a biological activator containing reactor and a separating membrane, in which the liquid flow containing a fluidized biocatalyst, reacting agent(s) and product(s) is circulated while exerting the biological reaction, as described in U.S. patent application Ser. No. 205,955.

Accordingly, it is one object of the invention to provide a continuous feeding method wherein neither an extraordinarily high pressure nor an extraordinarily low pressure occurs in the bioreactor, and therefore no cavitation occurs in the circulating pump of the closed tubular bioreactor.

It is another object of the invention to provide a method for continuously and constantly feeding substrate into a tubular bioreactor in which an influent of the product liquid (that is, an amount of the liquid passing through a membrane) can be always balanced with a substrate (that is, an amount of the feed).

The foregoing and other objects of the present invention can be attained by the following description.

DETAILED DESCRIPTION OF PREFERRED EMBODIMENTS

Figure 1:
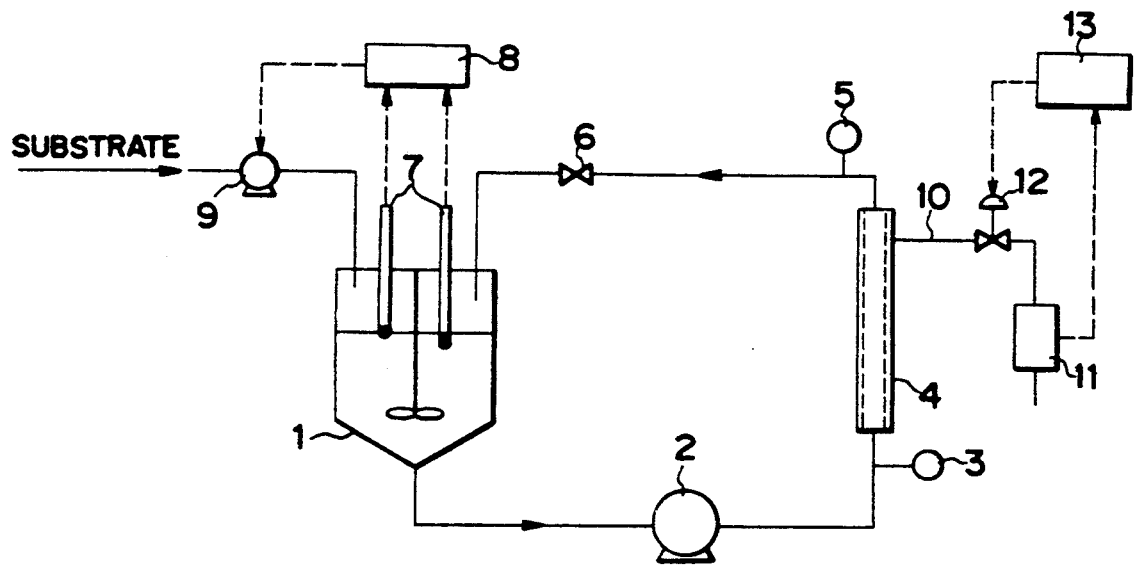
FIG. 1 is a sectional view of the prior art continuous bioreacting system for a biological reaction.
Figure 2:
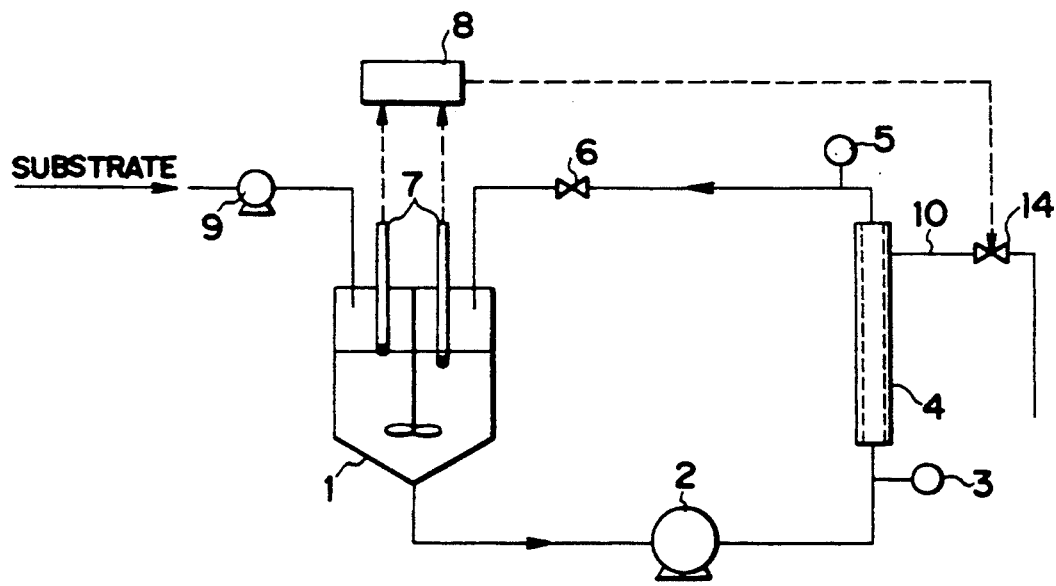
FIG. 2 is a sectional schematic view of the other one of the prior art continuous bioreacting system for a biological reaction.

The bioreactor used in accordance with the present invention constitutes a tubular structure in the form of a closed loop, comprising tubing(s), a circulating pump and tubular membrane element(s) (membrane modules). Within the bioreactor a biological process can be continuously carried out to produce useful product(s) that can be continuously separated and discharged from the reaction flow or the bioreactor at the same time. The continuous separation of the product from the reaction mixture is achieved by the tubular membrane modules mounted on the loop structure in place of at least a portion of the walls of the tubing.

In accordance with the present invention, the substrate(s) is continuously and constantly fed into a tubular bioreactor having a closed circuit structure, in which a reaction mixture containing a fluidized biocatalyst (enzyme or microorganism), substrate(s) and product(s) is circulated (or recurred). It should be noted that the useful material or product is produced by a biological reaction.

The bioreactor structure comprises a tubing, formed from tubular hollow vessels, a circulating pump and porous tubular membrane module(s), through which said useful product can permeate so as to collect and discharge a liquid containing said product through an outlet. The outlet is mounted on the wall of the outer tube coaxial about the membrane module. The membrane modules are provided in place of at least a portion of the walls of the loop structure and further, the structure is provided with at least one inlet for feeding the substrate(s). In accordance with the present invention, the substrate(s) are fed from an inlet provided at the suction position (at position near to and upstream of said circulating pump) in a circular tubular structure of said bioreactor, by means of the suction power at that position. As a result, the flow rate of the liquid passing through the membrane modules can be adjusted to the desired level by means of an adjusting valve mounted at a position downstream of the membrane modules in said discharging outer tube.

In accordance with the present invention, the method for controlling the flow rate of the substrate further comprises the steps of measuring the flow rate of the liquid passing through the membrane modules by measuring a flow rate of the substrate at a desired level based upon the microbial or enzymatic reaction rate; adjusting a flow rate of said substrate at a level predetermined on the basis of the effective volume of said tubular bioreactor so as to give desired dilution rate in the circulating liquid, and adjusting a flow rate of the liquid passing through said membrane modules, to a level giving the predetermined flow of the substrate(s). It should be noted that the flow rate is measured by conventional means mounted on the outer tube.

The membrane module used in the bioreactor may comprise a number of small porous membrane tubes bundled in tubular form, such that the reaction mixture flows in the inner hollows of said small porous membrane tubes. Preferably, the total sectional area of all inner hollows of the small porous membrane tubes substantially equals the inner sectional area of the other connecting tube or pipe.

The tubular member surrounding and enclosing the bundle of the small membrane tubes, and provided with an outlet for discharging the product, is coaxial about the bundled tubular form of the membrane module. Further, the connecting structure between the tubular membrane module and the other hollow tube or pipe comprises a similar structure to that of a heat exchanger in a multiple pipe tubular form.

The closed circuit structure is provided with a means of circulating the reaction mixture containing the substrate, the fluidized biocatalyst and the product. It is further provided with the tube(s) which connect the parts constituting the above circuit structure. Within the closed circuit structure the reaction mixture continuously flows, and circulates without a stirring reactor.

While a pump is shown in the drawings, it may be any device capable of generating the liquid circulating power to make the liquid circulate in the closed loop circuit.

Further, a heat exchanger can be mounted in the bioreactor so as to adjust the temperature in the bioreactor within a predetermined temperature range adapted for biological activity.

Figure 3:
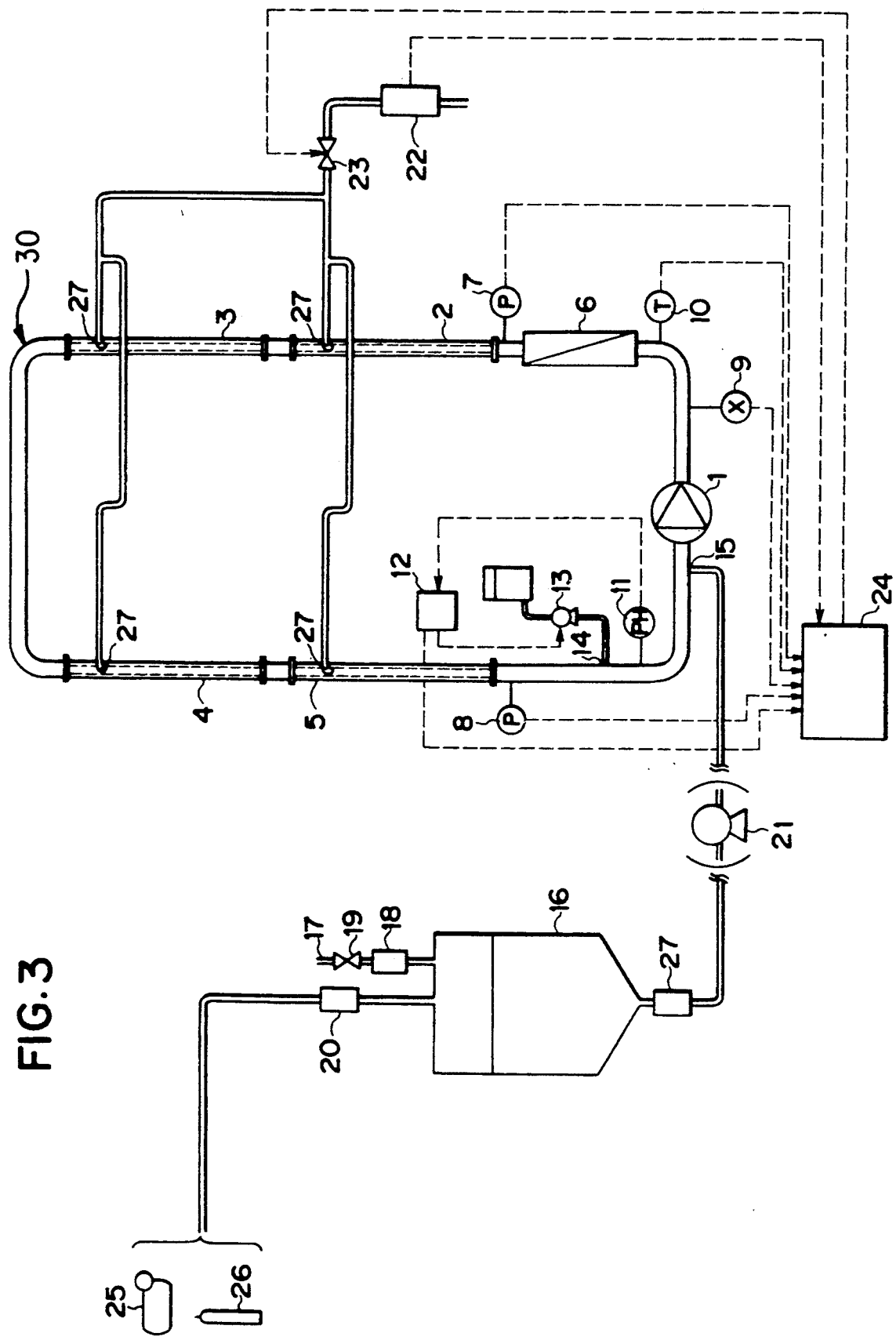
FIG. 3 is a sectional schematic representation of a tubular bioreactor into which substrate is controlledly fed for biological reaction in accordance of the present invention.
Figure 4:
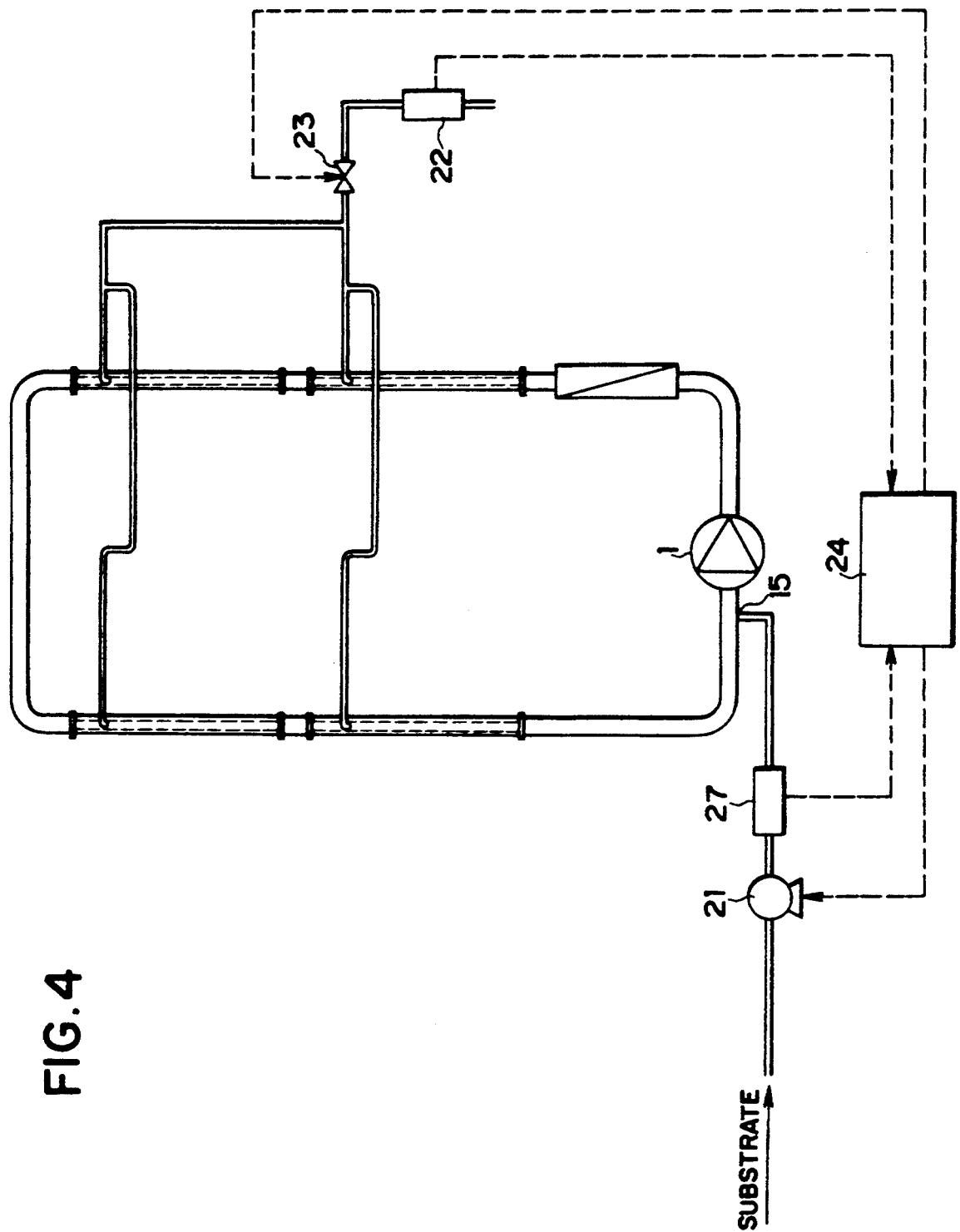
FIG. 4 is another sectional schematic representation of another embodiment of the tubular bioreactor to which substrates are continuously and controlledly fed in accordance of the present invention.

Referring now to the drawings, a section illustration of the bioreactor system of the present invention is presented in FIGS. 3 and 4.

FIG. 4 illustrates a basic embodiment of the inventive tubular bioreactor, wherein, like reference characters designate like or corresponding parts as shown in FIG. 3.

The position of each element or component constituting the closed circuit structure is not restricted to those shown in the drawings including FIGS. 3 and 4.

Further, tubular membrane modules 2 to 5 can be substituted in place of the part(s) of the tubing, thereby enhancing the separating efficiency of the product from the reaction mixture.

Generally speaking, when the concentration of the substrate in the medium is lower than the saturation value during the biocatalytic reactions, the reaction rate is dependent on the concentration of the substrate. The saturation value is a measure of the concentration of the substrate in the media, that is, a value for the saturation concentration of the microbial or enzymatic reaction. In turn, when the concentration of the substrate is higher than the saturation value, the reaction rate is constant and independent from the concentration of the substrate. Therefore, in the continuous operation of such a reaction, a lower feed rate of the substrate leads to a lower rate of the reaction. Consequently, when the feed rate of the substrate becomes higher than the necessary (optimum) value, the excess of the substrate will flow out from the reactor. Accordingly, it is necessary to optimize the feed rate of the substrate in the tubular bioreactor, so that the reaction rate is maximized and the utilization efficiency of the substrate is maximized. On the other hand, since the reaction and the separation of the product from the reaction mixture (comprising the substrate, the fluidized biocatalyst and the product) are carried out at the same time in the tubular bioreactor by using membrane modules in place at least of a portion of the wall of the circular structure, the flow rate of flowing out the product mixture is controlled by the permeating rate of the membrane modules. Therefore, it is necessary to control the permeating rate by any method, in order to optimize the feed rate of the substrate.

Since the tubular bioreactor is in a closed loop structure, the pressure in the tubular bioreactor will become extraordinarily high when the feed rate of the substrate is higher than the flow rate of the liquid passing through the membrane modules. Alternatively, if the feed rate of the substrate is lower than the flow rate of the liquid passing through the membrane modules, the pressure becomes extraordinarily low; as a result, cavitation in the pump will occur.

The liquid rich in the product and not containing the fluidized biocatalyst passes through the membrane modules and an amount of the liquid, equal to that of the feed will be discharged from the outlet. The fluidized biocatalyst is kept in the tubular circuit of the bioreactor because the fluidized biocatalyst cannot pass through the membrane modules. Therefore, the substrate can be continuously processed.

The system of feeding a substrate into a tubular bioreactor is illustrated referring to FIG. 3.

A tubular bioreactor comprises a circulating pump 1, and a tubular hollow vessel 30 which includes membrane modules 2, 3, 4 and 5, a heat exchanger 6 and a tubing connecting those elements.

As shown in FIG. 3, the tubular bioreactor includes pressure sensors 7 and 8, a turbidity sensor 9, a temperature sensor 10, a pH sensor 11, a pH controller 12, a chemical pump 13, an inlet of chemicals 14, an inlet of substrates 15, a substrate tank 16, a pressure adjusting opening 17, a filter 18, a pressure adjusting valve 19, a filter 20, a pressure pump 21, a flow rate measuring means 22, a flow adjusting valve 23, a computer 24, a compressor 25 and a gas cylinder 26.

The membrane modules (2, 3, 4, 5) contain a necessary number of cylindrical pressure ceramic membranes. The reaction liquid is circulated by a circulating pump 1 through a closed loop circular structure, in which cross flow filtration is carried out at and through membrane modules 2, 3, 4, 5 to separate the reaction product from a biological catalyst containing liquid.

The circulating pump 1 will establish a given pressure to circulate the reaction liquid and to carry out cross flow filtration. The pump 1 also maintains a necessary flow rate for passing the liquid through the membranes. The pressure upstream of the membrane module 2 is measured by a pressure sensor 7, and the pressure downstream of the membrane module 5 is measured by a pressure sensor 8 so as to accomplish monitoring of the operation. The temperature in the bioreactor is adjusted by controlling the flow rate of water flowing into a heat exchanger for maintaining the temperature measured at a temperature sensor 10 at a constant temperature. The heat generated by the circulating pump 1 and the biologically catalyzed reaction will raise the temperature in the bioreactor. A temperature sensor 10 is provided, as shown in FIG. 3, between a circulating pump 1 and a membrane module 2, rather near to circulating pump 1. Further, a heat exchanger 6 is provided near membrane module 2 in the loop circular structure.

The closed loop structure of the tubular bioreactor can be covered with an insulating material so as to avoid any influence from the outside or the atmospheric temperature, thereby maintaining a constant temperature in the bioreactor.

The pH of the circulating liquid can be adjusted by a pH controller 12 in which an alkali or acid solution is put into the bioreactor from an inlet 14 by a chemical pump 13, on the basis of the measurement of pH value by a sensor 11. The inlet 14 is mounted at a position of lower pressure in the circular structure (i.e. between the membrane module 5 and a circulating pump 1 in the loop circular structure) so as to minimize the loading pressure of the solution from a chemical pump 13. Because it will take time to accomplish a complete mixture of the poured alkali or acid solution in the reaction mixture, the pH sensor 11 is mounted at the upper stream in the circular structure from an inlet 14.

Parameters such as temperature, pressure, pH, concentration of bioactive catalyst measured by temperature sensor, pressure sensor, pH sensor and turbidity sensor 9 are monitored and memorized by a computer 24.

Substrate is fed from a substrate inlet 15 mounted at a position as near as possible to a circulating pump 1, in the loop circular structure between a membrane module 5 and a circulating pump 1. At this position the suction power is highest, because of the low pressure in the loop circulating tube caused by the power of the circulating pump 1. Therefore, the substrate can be spontaneously and automatically suctioned, or put into the loop circulating bioreactor, in the same amount as that of the liquid passing through the membrane modules. A substrate tank 16 is sealed to preclude harmful bacteria, and an inner pressure adjusting opening 17 has a filter 18 and a pressure adjusting valve 19. A sterilized substrate is furnished through a filter 20 into a substrate tank 16 without any harmful bacteria contamination.

The feed rate of the substrate can be raised by feeding the substrate with pressure at a level allowable to the bioreactor so as to raise the pressure in the bioreactor. The necessary pressure can be attained by using a compressor 25 or a steel gas cylinder 26 to supply a pressure gas through a filter 20, or alternatively by equipping a pressure pump 21 in the piping between a substrate tank 16 and a substrate inlet 15, so as to attain the necessary pressure in the bioreactor. The pressure pump should be a centrifugal pump that can be operated in closed form, because a volume pump will generate an imbalance between the amount of the substrate and that of the discharged liquid. This is a result of the constant flow rate of the liquid passing through the membrane modules in the bioreactor.

The flow rate of the liquid passing through the membrane modules can be regulated at a given level by operating a flow adjusting valve 23 in terms of the feedback controlled by a computer 24 on the basis of the measured value of the flow rate by a measuring means 22. For example, a flowmeter or a load cell maybe utilized. The flow rate, the total flow of the liquid passing through the membrane modules, and the regulating voltage for the flow adjusting valve are monitored and memorized by a computer 24.

The tubular bioreactor is in a closed loop structure, and the pressure in the tubular bioreactor will become extraordinarily high when the feed rate of the substrate is higher than the flow rate of the liquid passing through the membrane modules. Alternatively, if the feed rate of the substrate is lower than the flow rate of the liquid passing through the membrane modules, the pressure becomes extraordinarily lower; as a result, cavitation will occur in the pump. Therefore, it is necessary that balance should be established between the flow rate of the liquid passing through the membrane modules and the feed rate of the substrate. Therefore, the dilution rate, as referring to a parameter for the operation of this bioreactor, can be controlled at a desired value. Hereinafter, the term "dilution rate" means "the value of the substrate feed divided by the effective volume of the tubular bioreactor", and therefore, corresponds to a reversal of the retention time. The effective volume of the bioreactor corresponds to the total volume of the liquid to totally fill in the closed loop structure of the tubular bioreactor.

In order to maintain the reaction efficiency at a maximum level, and further to maintain the concentration of the reaction product at a constant value, the dilution rate should be optimized on the basis of the parameters in term of the reaction state.

The inventors first contemplate a method of independently controlling both the flow rate of the liquid passing through the membrane modules and the feed rate of the substrate such that the flow rate and feed rate are balanced or equalized with each other. This method can be carried out in the apparatus shown in FIG. 4.

FIG. 4 illustrates a simplified embodiment of the inventive feeding system. Each of flow rates of the liquid passing through the membrane modules and substrates is adjusted independently so that the amounts of the outflow and the substrate inflow are balanced and equalized.

The flow rate of the liquid passing through the membrane modules is measured by using a flow measurement means 22, such as a flowmeter or a load cell, and the signals from the measurement means 22 are inputted into a computer 24. The computer 24 then operates a flow adjusting valve 23 in terms of feed back control to adjust the flow rate at given value.

The feed rate of the substrate is measured by using a flow measurement means 27. The signal is put into a computer 24, which operates a feed pump 21 in terms of feed back control, so as to adjust the output from the pump 21 at the same value as the flow of the liquid passing through the membrane modules. The inlet 15 may be mounted at any position in the circular loop structure, but the output pressure from the pump 21 should be higher than the operating pressure in the loop structure of the bioreactor.

However, in this operation, it is very difficult to strictly equalize the feed rate to the flow rate of the liquid passing through the membrane modules, and further, both will gradually depart from each other during the passage of time when the operation continues for a long period of time.

The inventive method of feeding the substrate utilizes the phenomenon that the pressure at the position near the pump in the closed loop structure will be lowered due to the suction power by the pump. This is a result of a portion of the liquid filling in the inner space of the bioreactor being discharged from the bioreactor by passing through the membrane modules, and then, it tries to assume its original pressure. The substrate will be fed automatically and spontaneously in the same amount as that of the liquid passing through the membrane modules, and then, the control of only the amount or the flow rate of the liquid passing through the membrane modules.

In the embodiment shown in FIG. 3, the flow rate of the liquid passing through the membrane modules 2, 3, 4, 5 can be adjusted to a given level by feedback control of flow adjusting valve 23. The feedback is controlled by a computer 24 on the basis of the measured values of the flow rate of the liquid passing through the membrane modules, as measured by a flow measuring means 22, for example, a flowmeter or a load cell.

In the following examples, the invention is further explained with reference to the high concentration and continuous fermentation using a lactic acid bacteria, and controlling the substrate feed flow in the tubular bioreactor. The bioreactor used for these examples is shown in FIG. 3.

The components shown in FIG. 4 are simplified. The circulating pump 1 is a volume-type rotary pump which can provide pressure and circulation to the reaction mixture in the bioreactor. Also, the bioreactor shown in FIG. 4 does not need members or components for generating pressure in the bioreactor. Accordingly, the bioreactor of FIG. 4 does not include a pressure pump 21, a compressor 25, a steel gas cylinder 26, an inner pressure adjusting opening 17, a bacteria filter 18, or a pressure adjusting valve 19, as shown in FIG. 3. The measurement of means 22 shown in FIG. 4 for measuring the amount or flow rate of the liquid passing through the membrane modules, may be a load cell. Further, a load cell 27 may be provided at the substrate tank so as to measure the substrate feed rate. The other components in FIG. 4 are the same as in FIG. 3.

The effective volume of the bioreactor shown in FIG. 4 is 2.6 liters.

EXAMPLE 1

Constant Feed Flow

A flow adjusting valve 23 as shown in FIG. 3 was adjusted by a computer 25 on the basis of the measured value of the flow rate of the liquid passing through membrane modules. The value was measured by a flow measurement means 22 in a load cell. The value was adjusted so that the flow rate of the liquid passing through the membrane modules should be at the given value of $F_p=0.835$ (liters/hour) in the dilution rate of 0.32 (1/hour). The substrate was suctioned or fed from an inlet 15, at the flow rate corresponding to $F_p=0.832$ (liters/hour) into a tubular bioreactor. This was confirmed by a load cell 27 provided at a substrate tank 27 in FIG. 3.

EXAMPLE 2

Substrate Feed Rate Proportional to Organism Concentration

The substrate was fed at a feed rate proportional to the concentration of lactic acid bacteria in order to culture the lactic acid bacteria in the circular bioreactor.

The feed rate of the substrate is equal to the flow rate of the liquid passing through membrane modules F. Therefore, $F_p = a \times X$ wherein, a is a proportional constant, and X is the concentration of the lactic acid bacteria in the liquid. The concentration X of lactic acid bacteria was measured by a turbidity sensor 9, and the flow rate of the liquid passing through the membrane modules was calculated from the measured value of turbidity by a computer 24. Then, a flow adjusting valve 23 was controlled by the computer 24 on the basis of the calculated flow rate.

$X_0$ is the concentration of the bacteria when the fermentation is initiated. Because the feed rate of the substrate is proportional to the concentration of the lactic acid bacteria for the fermentation, X is the concentration of the bacteria at the time t from the initiation of the fermentation, and the rate of proportional proliferation of the bacteria is $\mu$.

$$X = X_0 exp(-\mu t)$$

Therefore, $F_p = 0.0832 exp(-\mu t)$

From this equation, it is evident that the concentration X of the bacteria will increase exponentially. Then, it was confirmed that the flow rate of the liquid passing through the membrane modules, as measured by a load cell 22, was established to be the same as the feed rate of the substrate.

The following features are attained by the inventive feeding method for the tubular bioreactor:

A balance can be attained between the amount of the liquid passing through the membrane modules and the amount of the substrate. Therefore, the dilution rate in the bioreactor can be controlled at an optimum value or be optimized by constantly feeding the substrate into the bioreactor.

The reaction efficiency in the bioreactor can be maximized, and the concentration of the reaction product can be maintained at constant value, during the operation of the bioreactor.

The amount of the substrate feed, corresponding to the amount of the liquid passing through the membrane modules, can be automatically spontaneously fed in the bioreactor. Therefore, only the control of the flow rate of the liquid passing through the membrane modules leads to the control of the substrate feed rate at the desired value, and thereby the optimization of the dilution rate.

An embodied usage of the inventive method of operating the tubular bioreactor may include a lactic acid fermentation by utilizing glucose with a microorganism such as Lactobacillus. Another usage may include alcoholic fermentation using yeast organism.

The method of feeding the substrate into the tubular bioreactor enables simplification so that it is economical and uncostly to establish continuous and constant operation. The continuous operation needs continuous and constant feeding of the substrate(s). This can be attained by continuous and constant removal of the product through the membrane modules mounted on the wall of the closed loop circular structure of the bioreactor.

Although the invention has been described in its preferred embodiments, it is understood that the present disclosure of the preferred embodiments may be changed with regard to the details of construction, and the combination and arrangement of parts may be varied, without departing from the spirit and the scope of the invention as hereinafter claimed.

What is claimed is:

1. A method of feeding a substrate into a tubular bioreactor of a closed loop, within which an aqueous liquid mixture comprising a substrate, fluidized biocatalyst, and product is continuously circulated, comprising:

a tubular hollow vessel forming said closed loop in which said aqueous liquid mixture can be smoothly circulated;

tubular membrane modules constituting at least a portion of an inside wall of said tubular hollow vessel, through which said product permeates to an outlet line having an adjusting valve for adjusting an amount of discharge of aqueous liquid mixture;

a circulating means for continuously circulating said aqueous liquid mixture in said tubular hollow vessel; and an inlet for feeding said substrate from a feed line to said tubular hollow vessel, said inlet being mounted at a position just upstream of said circulating means;

wherein said method comprises the steps of:

(a) applying pressure to said feed line to create pressurized liquid in said tubular hollow vessel;

(b) feeding said substrate from said inlet into said tubular hollow vessel by means of suction power generated at the corresponding position in said tubular hollow vessel along said closed loop; and (c) adjusting the flow rate of aqueous liquid mixture passing through said membrane modules as well as the feed rate of said substrate into the closed loop at a desired level, by adjusting the opening of said adjusting valve mounted on said outlet line, at a level to give a predetermined feed rate of the biocatalyst, discharge rate of the aqueous liquid mixture falling out from said outlet line, and concentration of the biocatalyst, so that the yield of said product and the reaction rate are maximized.

2. A method of feeding a substrate into a tubular bioreactor as claimed in claim 1, wherein one of a gas cylinder, compressor, and combination of cylinder and compressor are used to apply pressure to said feed line.

3. A method of feeding a substrate into a tubular bioreactor as claimed in claim 1, wherein the flow rate of the aqueous liquid mixture passing through said porous tubular membrane module is additionally raised by raising the pressure in said tubular hollow vessel by providing a pressure pump to said feed line of said substrate.

4. A method of feeding a substrate into a tubular bioreactor as claimed in claim 1, wherein a heat exchanger is provided on said closed loop to adjust the temperature in said tubular hollow vessel.

5. A method of feeding a substrate into a tubular bioreactor in a closed loop which comprises a closed loop path in which an aqueous liquid mixture containing media, substrate, biocatalyst and product continuously flows, and is smoothly circulated by circulating means; said closed loop path being defined by the interior wall of tubular vessels comprising:

(a) annular conduits for smoothly circulating said aqueous liquid mixture;

(b) porous tubular membrane modules which have hollowed micro membrane tubes in which said aqueous liquid mixture smoothly flows, said porous tubular membrane modules forming at least a portion of said closed loop path, said product permeating through said porous tubular membrane modules, and each of said modules having one end connected to an end of one of said annular conduits and a second end connected to an end of another of said annular conduits;

(c) a circulating means installed in a portion of one of said annular conduits through which said aqueous liquid mixture is pumped for effecting circulation thereof;

(d) an outlet having an adjusting valve for discharging the product from the bioreactor, said outlet being mounted on the outer surface of said porous tubular membrane modules; and (e) an inlet for feeding the substrate to the closed loop path, said inlet being mounted on a wall of one of said annular conduits just upstream of the circulating means, comprising the steps of:

(a) applying pressure to a feed line to develop pressurized liquid in the closed loop path;

(b) feeding the substrate from said inlet into said closed loop path by means of suction power or negative pressure generated at a corresponding position in said closed loop path along with the closed loop path;

(c) adjusting the flow rate of said aqueous liquid mixture passing through said porous tubular membrane modules and the feed rate of said substrate into said closed loop path at a desired level, by adjusting the opening of said adjusting valve at a level to give a predetermined flow rate of said substrate on the basis of the biocatalytic reaction rate of the biocatalyst, flow rate of said liquid flowing out from an outlet line, and concentration of said biocatalyst, so that the yield of said product and the reaction rate are maximized.

6. A method of feeding substrate into a tubular bioreactor of a closed loop, in which an aqueous liquid mixture comprising a substrate, fluidized biocatalyst and product is circulated in said tubular bioreactor for continuously propagating a biocatalytic reaction, and continuously recovering products of said propagation; said tubular bioreactor comprising a tubular closed loop circulating structure defined by the interior of tubular members; comprising (a) a feed line for feeding a substrate medium to said tubular closed loop circulating structure;

(b) annular looped ducts in which tubular closed loop circulating said aqueous liquid mixture and media continuously flows, and is smoothly circulated by a circulating means;

(c) porous tubular membrane modules which have a number of hollow micro membrane tubes in which said substrate medium flows, said porous tubular membrane modules forming at least a portion of said tubular closed loop circulating structure, said product flowing through said porous tubular membrane modules;

(d) an outlet for continuously discharging product from the tubular bioreactor, said outlet being mounted on the outer surface of said porous tubular membrane modules and connected to an outlet line;

(e) an inlet for feeding substrate to said tubular closed loop circulating structure, said inlet being mounted on a wall of said annular ducts; and (f) a circulating means installed in said annular looped ducts just downstream of said inlet, said method comprising the steps of:

(a) applying pressure to said feed line to develop pressurized liquid in said annular looped ducts;

(b) feeding said substrate medium from said inlet into said annular looped ducts, by means of suction power generated at a corresponding position in the annular looped ducts along the closed loop; and (c) adjusting the flow rate of said liquid passing through said porous tubular membrane modules and the feed rate of said substrate into the circulating flow path at the desired level, by adjusting the opening of an adjusting valve mounted on the outlet line, at a level to give a predetermined feed rate of the substrate on the basis of the biocatalytic reaction of the biocatalyst, a discharge rate of the liquid flowing out from the outlet line, and concentration of the biocatalyst, so that the yield of said product and said reaction rate are maximized.

7. A method of feeding substrate into a tubular bioreactor of a closed loop, in which an aqueous liquid mixture comprising the substrate, fluidized biocatalyst and product is smoothly circulated in the tubular bioreactor, and which structure comprises a tubular hollow vessel forming a closed loop circulating flow path defined by the interior surface of tubular members in which the aqueous liquid mixture flows, and is smoothly circulated in a closed loop form; porous tubular membrane modules which have a number of hollowed micro membrane tubes in which said aqueous liquid mixture flows, which porous tubular membrane modules form at least a portion of the inside wall of said closed loop circulating flow path, through said number of hollow micro membrane tubes of said porous tubular membrane modules the product permeates; an outlet for continuously discharging the product from the tubular bioreactor, said outlet being mounted on the outer surface of the porous tubular membrane modules, and connected to an outlet line; an inlet for feeding the substrate into the closed loop circulating flow path, said inlet being mounted on a wall of the portion of the tubular members and a circulating means for smoothly circulating the aqueous liquid mixture in said tubular hollow vessel;

said method comprising the steps of:

(a) applying pressure to the feed line to pressurize the liquid in the tubular hollow vessel;

(b) feeding the substrate from the inlet into said tubular hollow vessel, by means of suction power generated at the corresponding position of the tubular hollow vessel along the closed loop;

(c) adjusting the flow rate of said liquid passing through said porous tubular membrane modules as well as the feed rate of the substrate into the closed loop circulating flow path at a desired level, by adjusting the opening of an adjusting valve mounted on the outlet line at a level to give a predetermined feed rate of the substrate on the basis of the biocatalytic reaction of the biocatalyst, a discharge rate of the liquid flowing out from the outlet line, and concentration of the biocatalyst, so that the yield of the product and the reaction rate are maximized.

* * * * *